(12) United States Patent
Richards et al.

(10) Patent No.: US 7,211,265 B2
(45) Date of Patent: May 1, 2007

(54) VACCINATION MODALITIES

(75) Inventors: David Grant Richards, Frankston North (AU); Wayne Keith Jorgensen, Brisbane (AU); Norman Porter Stewart, Harvey Bay (AU)

(73) Assignees: Eimeria Pty. Limited (AU); The State of Queensland through the Department of Primary Industries (AU); Rural Industries Research and Development Corporation (AU)

( * ) Notice: Subject to any disclaimer, the term of this patent is extended or adjusted under 35 U.S.C. 154(b) by 0 days.

(21) Appl. No.: 10/841,476

(22) Filed: May 10, 2004
(Under 37 CFR 1.47)

(65) Prior Publication Data
US 2005/0008659 A1 Jan. 13, 2005

Related U.S. Application Data

(63) Continuation of application No. 09/647,098, filed as application No. PCT/AU99/00232 on Mar. 30, 1999, now abandoned.

(30) Foreign Application Priority Data
Mar. 30, 1998 (AU) ..................................... PP 2683

(51) Int. Cl.
*A61K 39/012* (2006.01)
*A61K 39/00* (2006.01)
*A01N 63/00* (2006.01)
*C12N 1/00* (2006.01)

(52) U.S. Cl. ............... 424/271.1; 424/93.1; 424/184.1; 435/243

(58) Field of Classification Search ............. 424/271.1, 424/93.1, 184.1; 435/243
See application file for complete search history.

(56) References Cited

U.S. PATENT DOCUMENTS 4,438,097 A 3/1984 Shirley
5,055,292 A 10/1991 McDonald

FOREIGN PATENT DOCUMENTS

WO WO 94/16725 8/1994

OTHER PUBLICATIONS

Shirley et al, *The Veterinary Record*, 137(18):453-457 (1995).
Shirley et al, *Br. Vet. J.*, 148(6):479-499 (1992).
Jorgensen et al, *Aust. Vet. J.*, 75(8):592-595 (1997).
Calnek, *Dev. Biol. Stand.*, 52:401-405 (1982).

*Primary Examiner*—Nita Minnifield
*Assistant Examiner*—Vanessa L. Ford
(74) *Attorney, Agent, or Firm*—Sughrue Mion, PLLC

(57) ABSTRACT

Vaccines for the prevention and/or treatment of *Eimeria* infection including one or more strains of *E. maxima* ARI-73/97, *E. acervulina* ARI-77/97, *E. tenella* ARI-11/98, *E. necatrix* MCK01 and/or *E. necatrix* ARI-MEDNEC$_3$+8 are described. *Eimeria* selected from *E. maxima* ARI-73/97, *E. acervuina* ARI-77/97, *E. tenella* ARI-11/98, *E. necatrix* MCK01 and/or *E. mecatrix* ARI-MEDNEC$_3$+8 are also described.

10 Claims, No Drawings

VACCINATION MODALITIES

CROSS-REFERENCE TO RELATED APPLICATIONS

This application is a Continuation of U.S. application Ser. No. 09/647,098, filed May 2, 2001, now abandoned which in turn is a 371 of PCT/AU99/00232, filed Mar. 30, 1999, the disclosure of each of which is incorporated herein by reference.

This invention relates to vaccination strains of *Eimeria* and vaccines including the same.

Coccidiosis is a disease of major economic importance for the intensive poultry industry conducted around the world. The causative agent is *Eimeria*, a protozoan parasite.

In the chicken seven different species of *Eimeria* have been identified, namely *E. maxima, E. acervulina, E. necatrix, E. tenella, E. mitis, E. praecox* and *E. brunetti*. Not all of these species may be present in any particular country or region. *E. maxima, E. acervulina, E. necatrix* and *E. tenella* are prevalent species of *Eimeria*.

*Eimeria* have a complicated life cycle, details of which are well described, for example, in *Poultry Coccidiosis: Diagnostic and testing procedures*, Second Edition, Pfizer Inc. Briefly, when a sporulated (infective) coccidial oocyst is ingested, sporozoites are released to initiate asexual and sexual cycles that lead to the development of thousands of new oocysts, which are shed in the faeces. These oocysts sporulate shortly thereafter and then are infectious for other birds. A single sporulated oocyst may give rise to as many as ten thousand progeny. *Eimeria* produce lesions in the gut by destruction of the epithelial cells in which they develop and multiply, and by trauma to the intestinal mucosa and submucosa.

The various species of *Eimeria* (which may otherwise be referred to as coccidia) can be identified by microscopic features of oocysts (size, shape, length and width), the preferred locations of coccidia in the gut, the nature of the lesions produced, prepatent period, sporulation times and reproductive index, DNA testing and lack of cross protection between species. Identification of a particular species' infection can therefore be made with general accuracy based on any one or more of these features.

The clinical signs of coccidiosis include diarrhoea, which may be mucoid or bloody and dehydration. These symptoms are generally followed by ruffled feathers, anaemia, listlessness, loss of weight, retraction of the head and neck and somnolence. Coccidiosis in laying hens is usually observed by a drop in egg production. Infected growing birds, soon cease to grow satisfactorily. With highly virulent strain mortality in chickens is generally very high.

According to 1997 figures about twenty billion birds at reared each year across the world. Control of coccidiosis in such a large bird population has generally been by anti-coccidial drugs which have in the whole been effective. Not surprisingly, however, drug resistance is now a problem with an increasing number of *Eimeria* strains being resistant to drugs. The development of drug resistant, highly virulent *Eimeria* strains has the potential to devastate the poultry industry.

The possible control of coccidiosis by vaccination has received interest over the years, without any great success. Attempts to develop genetically engineered or sub-unit vaccines have so far been unsuccessful (Shirley, 1992, *Br. Vet. J.*, 148:479). A living vaccine, (Paracox, Pitman-Moore) containing oocysts from attenuated strains of coccidia has been used in Great Britain (Farrent, 1992, *Poultry World*, 4:11).

The Paracox live vaccine referred to above is based on precocious lines of various *Eimeria* species. Precocious lines of *Eimeria* are populations that complete their endogenous life cycle in the host more quickly than wild-type stains. The process of this selection was first described by Jeffers (1975, *J. Parasitol.* 61, 1083–1090). Serial passage in the chicken of the first oocyst produced during infection yields parasites characterised by an abbreviated life cycle, and possibly some attenuation of virulence. Problems associated with precocious lines are failure to protect against virulent *Eimeria* species, poor reproductive capacity such that it is not feasible to produce a vaccine using such strains, and issues of stability associated with attenuation, and maintenance of infectivity. For example, Shirley and Bellatti (1988, *Re. Vet. Sci.*, 44:25–28) describe a precocious line of *E. maxima* which protected poorly against challenge with virulent heterologous strains.

The present inventors have surprisingly produced vaccine strains of *E. maxima, E. acervulina, E. tenella* and *E. necatrix*, which are strongly protective against virulent strains from their respective species, grow at a rate which allow vaccine production, and are stable.

The geographical isolation of Australia from foreign coccidial diseases ensures the vaccines and vaccine strains described herein are unique, and therefore clearly is distinguishable from previously described precocious *Eimeria* strains.

In accordance with a first aspect of this invention, there is provided a vaccine which includes one or more strains of *E. maxima* ARI-73/97, *E. acervulina* ARI-77/97, *E. tenella* ARI-11/98, *E. necatrix* MCK01 and/or *E. necatrix* ARI-MEDNEC$_3$+8, or antigens of said one or more strains, in association with a veterinarially acceptable carrier or excipient.

The vaccine may contain other *Eimeria* species in addition to the referred to above. For example such additional species may be *Eimeria* stains of *E. brunetti; E. mitis*, and/or *E. praecox* and/or one or more or vaccine strains of *E. maxima, E. acervulina, E. necatrix* and/or *E. tenella*. Such additional strains, may not be as useful as the strains of the present invention, however they may still be advantageous components of a wide spectrum vaccine composition. The vaccine may also include at least one additional unattenuate strain. For example, one embodiment of a vaccine may contain *E. maxima* ARI-73/97, *E. acervulina* ARI-77/97, *E. tenella* ARI-11/98 and/or *E. necatrix* MCK01, and/or *E. necatrix* ARI-MEDNEC$_3$+8, and optionally one or more strains selected from *E. brunetti, E. mitis, E. mivati*, and/or *E. praecox* to give a multivalent vaccine. A preferred vaccine contains three to five vaccine strains of *Eimeria* sealed from *E. maxima* ARI-73/97, *E. acervulina* ARI-77/97, *E. tenella* ARI-11/98 and/or *E. necatrix* MCK01, and/or *E. necatrix* ARI-MEDNEC$_3$+8.

Additional strains of this invention having vaccine competency may be prepared by immunising birds with one or more of the strains *E. maxima* ARI-73/97, *E. acervulina* ARI-77/97, *E. tenella* ARI-11/98 and/or *E. necatrix* MCK01, and challenging the immunised birds with candidate strains from field isolates. Those stains which produce a large number of oocysts in the immunised birds, due to the vaccine not being cross protective for them (an unlikely event), are then subject to serial passage through birds to give a strain of the invention being strongly protective against virulent strains, having a reproductive rate which allows vaccine production, is stable, and sensitive to coccidiostatic drugs.

The organisms in the vaccines of this invention are in the form of whole and/or fractured or sporulated oocysts or sporocysts, or antigens thereof capable of inducing a protective immune response in a vaccinated bird. For convenience the term oocysts will be taken to mean sporulated oocysts, or a mixture of oocysts and sporulated oocysts. Oocysts are sporulated according to methods well known in the art, such as described by Jensen et al (1976) *The Journal of Parasitology* 2, 195–198, and 199–202. Sporulated oocysts or sporocysts are infective to birds by the oral, eye drop, nasal, or parenteral route. Antigens are generally proteins or peptides or fragments thereof (comprising for example 5 or more amino acids, such as from 5 to 50 amino acids). Carbohydrates, lipids, glycolipids and the like may also comprise antigens. Antigens are generally derived from the sporozoite stage of the organisms. Antigens may be produced by standard means including recombinant DNA technology, protein purification and other techniques as are well known in the art.

Veterinarially acceptable carriers include water, saline, buffered saline such as phosphate bufferd saline, or any other physiologically suitable medium. Carriers may include one or more suspending agents, thickening agents or preservatives including physiologically suitable gels, gelatins, hydrosols, cellulose or polysaccharide gums. Excipients may include vitamins, antibiotics and antifungals (virucides, bacteriocides and/or fungicides), surfactants and the like. Examples include one or more of streptomycin, linomycin, amphotericin, formaldehyde, chicken bile, sodium hypochlorite, sodium taurocholate, foetal calf serum and cystine hydrochloride.

Vaccines may comprise one or more *Eimeria* stains, and may contain from about 50 to about 50,000 sporulated oocysts per ml or more. The number of each *Eimeria* species present in the vaccine will generally be the same for the strain according to this invention. However, where additional vaccine strains are used, for example such as from *E. brunetti*, which are additional strains and not strains according to the present invention, a larger number of organisms may be proportionally used due to the less protective response compared with the strains of this invention. By way of example vaccines, such as for ocular or oral administration, a vaccine dose may comprise 15 to 500 sporulated oocysts.

The vaccines according to this invention may contain other vaccine components effective against other poultry disease. Examples include Marek's vaccine, Fowl Pox, Mycoplasma and Salmonella vaccines. Hence in another aspect of this invention there is provided a vaccine as hereinbefore described which includes vaccine components against one or more of Marek's disease, mycoplasma or Salmonella infection.

The vaccines according to this invention may be administered in ovo (for example from days 18–20 of incubation), to chicks and adult birds. The route of administration may be orally, intraocularly through the labrimal ducts, or by other known means of vaccine administration. As an example, a vaccine in an appropriate medium may be sprayed over a group of birds, sprayed on feed, administered as an eye drop, in feed water, as a part of prepared feed, or incorporated into a peck gel (such as sporulated oocysts in a gelatin matrix).

In another aspect this invention relates to vaccine *Eimeria* strains selected from the group *E. maxima* ARI-73/97, *E. acervulina* ARI-77/97, *E. tenella* ARI-11/98, *E. necatrix* MCK01, and/or *E. necatrix* ARI-MEDNEC$_3$+8. Preferably the strains are provided in the form of oocysts and/or sporulated oocysts.

Deposits of the *Eimeria* strains according to this invention were made with the Australian Government Analytical Laboratories (AGAL) a Budapest Treat Depository, of 1 Suakin Street, Pymble, New South Wales, 2073, Australia on 17 Mar. 1998, with the exception of *E. necatrix* ARI-MEDNEC$_3$+8 which was deposited on 30 Mar. 1999. Details are as follows:

| Strain | Accession No. |
| --- | --- |
| *E. maxima* ARI 73/97 | NM 98/02796 |
| *E. acervulina* ARI-77/97 | NM 98/02794 |
| *E. necatrix* MCK0I | NM 98/02797 |
| *E. necatrix* ARI-MEDNEC, +8 | NM 99/02118 |
| *E. tenella* ARI-11/98 | NM 98/02795 |

The *Eimeria* strains of the present invention may be reproduced by standard procedures in the art, such as the passage through naive uninfected fowl (i.e. not subject to *Eimeria* infection). Each strain may be produced in an uninfected fowl, oocysts recovered, optionally sporulated and then combined with a carrier and/or excipient. *Eimeria* strains may be grown in eggs according to standard procedures and oocysts recovered from the eggs. *Eimeria* strains can be routinely adapted to growth and reproduction in eggs by conventional means.

Oocysts and/or sporocysts of *Eimeria* strains according to the invention may be frozen (cryopreserved) in liquid nitrogen for storage according to methods known in the art such as according to M. W. Shirley. *Biotechnology Guidelines on Techniques in Coccidiosis Research* pp 97-(1995) ISBN 92-827-4970-3. By way of example sporocysts suspended in protein enriched media may be frozen in liquid nitrogen in the presence of dimethyl sulfoxide or glycerol, such as from 1 to 10% w/w.

This invention will now be described with reference to the following non-limiting examples:

EXAMPLE 1

A large number of *Eimeria* isolates from non-commercial (backyard) chicken flocks in Queensland of varying pathogenicity were collected. The isolates were generally mixed populations of *Eimeria* species however in most cases a single *Eimeria* species was the predominant pathogenic organism. Isolates were sorted by microscopic analysis into their respective species selected from *E. maxima, E. acervulina, E. tenella* and/or *E. necatrix*. Single oocysts from strains of each species were used to infect individual non-*Eimeria* infected birds generally in a volume of media, such as about 1 ml. Faeces from these birds were monitored for oocysts using the salt flotation technique (M. W. Shirley, *Biotechnology Guidelines on Techniques in Coccidiosis Research* pp 1–25 (1995) ISBN 92-827-4970-3) and oocysts recovered.

Individual *Eimeria* free birds were infected with up to 2000 oocysts of the purified strains to amplify them. These birds were euthanased and examined to confirm that the intestinal lesions were consistent with the species with which the bird was infected using the criteria mentioned above.

Attenuating the Strains

Strains were attenuated by serial passage by selecting for rapid development. Briefly, birds were infected with 1000–5000 parasites and monitored so that the first parasites voided were collected separately. This process was repeated a number of times (such as from 5 to 30 times) and parasites were progressively selected that developed faster; coinciding with this was their diminished ability to multiply in the chicken's gut and cause lesions. For many isolates precocious strains could not be produced, the stains were extremely pathogenic, showed poor growth rates, were drug resistant, and/or were unstable. These strains were discarded. On testing of the remaining strains for protection against challenge with a heterologous strain from the same species, many stains failed to provide cross protection within *Eimeria* species which is essential for vaccine development. From this work four vaccine strains of *Eimeria* were surprisingly produced from the species *E. maxima, E. acervulina, E. tenella* and *E. necatrix* all of which are strongly protective against virulent strains from their respective species, grow at a rate which allow vaccine production, were non-resistant to coccidiostatic drugs and are stable. The strains were designated *E. maxima* ARI-73/97, *E. acervulina* ARI-77/97, *E. tenella* ARI-11/98, *E. necatrix* ARI-MED-NEC$_3$+8 and *E. necatrix* MCK01.

Oocysts were sponged as follows: Faeces containing oocysts are placed into a solution of potassium dichromate. The dichromate acts as a bacteriostat. Air is bubbled through the solution. The process takes place in an incubator at 30° C. The process of sporulation is verified by observing the changes in the oocysts under a light microscope at a minimum of 100× magnification. Sporulation time is between 18 to 30 hours, depending on the species. After sporulation suspensions are placed into a refrigerator for vaccine preparation or storage.

Where there is less than 100 ml of faeces and dichromate, 50 ml of faecal suspension is placed into large Petrie dishes and placed into the incubator at 30° C. There is sufficient surface area and minimum depth to ensure oxygen diffuses into the mixture and sporulation occurs.

Strains were cryopreserved such as by immersion of oocysts in media (in an appropriate receptacle) into liquid nitrogen.

EXAMPLE 2

A series of trials were carried out using vaccines conning each of the strain produced in Example 1, combinations of from 2 to 4 of these strains as well as various combinations of strains according to Example 1 combined with other strains to give a vaccine. All these vaccines showed excellent protection against infection with heterologous *Eimeria* strains as well as treatment of *Eimeria* infection.

In one experiment sporocysts of *E. maxima* ARI-73/97, and *E acervulina* ARI-77/97 were combined in a vaccine with the Medichick strain of *E. necatrix*, and the Darryl strain of *E. tenella*. Birds were vaccinated with a vaccine containing 250 sporulated oocysts of each strain combined in 1 ml of saline.

Birds were maintained on solid floors within the wire cages for 21 days to assist reinfection with excreted oocysts. Feed and water were provided ad lib throughout the trial.

All birds were individually weighed and marked by wing clipping at time of challenge. Vaccinated and susceptible positive control groups of birds were either challenged with 6000 heterologous strain sporulated oocysts of Ingham's *Eimeria* strains of *E. tenella* and *E. necatrix*, and Medichick strains (*E. maxima* and *E. acervulina*) or 6000 oocysts of homologous strains. Weight gains and morbidity were compared between infected birds of the different treatment groups and uninfected control groups after 12 days. are shown in Table 1. ANOVA models (analysis of variance) appropriate to the designs were used to test the effects of treatments for statistical significance.

TABLE 1

Pen trial to compare mean live weight[1] gain in birds vaccinated as above and susceptible birds when challenged with 6 × 10³ oocysts each of Medichick strains of *E. acervulina* and *E. maxima* and Ingham's strains of *E. tenella* and *E. necatrix* or 6 × 10³ oocysts each of homologous strains of the 4 parasites.

| Treatment group (6 replicates) | Vaccination dose Quadravalent | Challenge dose[2] | Number of birds euthanased during challenge due to clinical symptoms | Mean weight gain (grams per bird)[3] |
|---|---|---|---|---|
| 1 | 25 oocysts of each of the 4 species | 6 × 10³ oocysts of each heterologous strain | 0/18 | 148[b] |
| 2 | 25 oocysts of each of the 4 species | 6 × 10³ oocysts of each homologous strain | 0/18 | 227[a] |
| 3 | nil | 6 × 10³ oocysts of each heterologous strain | 4/18 | 28[d] |
| 4 | nil | 6 × 10³ oocysts of each homologous strain | 3/18 | 78[c] |
| 5 | nil | nil | 0/18 | 201[a] |
| LSD (P = 0.05) | — | — | — | 36 |

[1]measured 12 days after challenge
[2]given on day 21 post vaccination
[3]Means within columns followed by common superscript letters are not significantly different at the 5% level.

As shown in Table 1 all vaccinated groups had significantly greater weight gains upon challenge with heterologous or homologous strains than unvaccinated birds. Clinical symptoms of *Eimeria* infection were not observed in the vaccinate birds, compared with the untreated birds.

EXAMPLE 3

A vaccine comprising *E. maxima* ARI-73/97 (15 oocysts). *E. acervulina* ARI-77/97 (25 oocysts), *E. tenella* ARI-11/98 (25 oocysts) and *E. necatrix* MCK01 (15 oocysts) per vaccine dose was prepared. The vaccine was used in a trial to measure body weight and immune stimulation of birds subject to immunisation, compared with control non-vaccinated birds. Of the four groups of birds tested, the first received the vaccine by eye drop, the second orally by feed, the third orally by drinking water, and the fourth group was a control. Birds were maintained in pens with solid floors and were reared on feed and water ad libitum, with light and heating being provided by lamps.

Post vaccination, all groups of birds vaccinated at one day old or at six days had similar growth rates when compared with unvaccinated controls. This indicates the vaccine does not effect growth rate underscoring its utility. Birds were challenged with *Eimeria* strains at 10× the number of oocysts used for vaccination.

Unvaccinated and challenged birds had a significantly higher oocyst production, which is characteristic for the spread of *Eimeria* infection amongst birds. The markedly reduced number of oocysts produced by vaccinated birds demonstrates a protective immunising response.

EXAMPLE 4

Vaccine compositions comprising sporulated oocysts of the aforementioned strains are prepared by suspension of sporulated oocysts in DulbeccoA phosphate buffered saline (Oxoid Laboratories, Heidelberg, Melbourne, Australia) at pH 7.4, containing 0.1% formaldehyde. Equal numbers of sporulated oocysts for each of strains *E. maxima* ARI-73/97, *E. acervulina* ARI-77/97, *E. tenella* ARI-11/98, and *E. necatrix* ARI-MEDNEC3+8, and/or *E. necatrix* MCK01 are used.

A vaccine for oral administration comprises 500 doses per ml comprising 90 oocysts per dose.

A vaccine for ocular administration comprises 40 doses per ml comprising 108 oocysts per dose.

Throughout this specification, unless the context requires otherwise, the word "comprise", or variations such as "comprises" or "comprising" or the term "includes" or variations thereof, will be understood to imply the inclusion of a stated element or integer or group of elements or integers but not the exclusion of any other element or integer or group of elements or integers. In this regard, in construing the claim scope, an embodiment where one or more features is added to any of claims is to be regarded as within the scope of the invention given that the essential features of the invention as claimed are included in such an embodiment.

The invention claimed is:

1. A vaccine comprising: (a) an effective amount of a combination of *Eimeria maxima* ARI-73/97 (deposit no. NM 98/02796), *Eimeria acervulina* ARI 77/97 (deposit no. NM 98/02794), and *Eimeria tenella* ARI 11/98 (deposit no. NM 98/02795), and optionally at least one member selected from the group consisting of *Eimeria necatrix* MCK01 (deposit no. NM 98/02797) and *Eimeria necatrix* ARI MEDNEC3+8 (deposit no. NM 99/02118); and (b) a veterinarially acceptable carrier or excipient, wherein said vaccine provides a protective immune response against heterologous *Eimeria* infection within 21 days post vaccination.

2. The vaccine according to claim 1, wherein each strain of *Eimeria* of said vaccine has a sporulation time of 18–30 hours.

3. The vaccine according to claim 1, wherein each strain of *Eimeria* of said vaccine is in the form of an oocyst, a sporulated oocyst, or a combination of both.

4. The vaccine according to claim 1, wherein said vaccine comprises between 15 and 500 sporulated oocysts.

5. The vaccine according to claim 1, wherein said vaccine comprises *Eimeria maxima* ARI 73/97 (deposit no. NM 98/02796), *Eimeria acervulina* ARI 77/97 (deposit no. NM 98/02794), *Eimeria tenella* ARI-11/98 (deposit no. NM 98/02795), *Eimeria necatrix* MCK01 (deposit no. NM 98/02797) and *Eimeria necatrix* ARI-MEDNEC3+8 (deposit no. NM 99/02118).

6. A method of inducing resistance to coccidiosis in a bird, said method comprising administering an effective amount of a vaccine of claim 1 to a bird, thereby inducing resistance to coccidiosis in a bird.

7. A method of inducing resistance to coccidiosis in a bird, said method comprising administering an effective amount of a vaccine of claim 2 to a bird, thereby inducing resistance to coccidiosis in a bird.

8. A method of inducing resistance to coccidiosis in a bird, said method comprising administering an effective amount of a vaccine of claim 3 to a bird, thereby inducing resistance to coccidiosis in a bird.

9. A method of inducing resistance to coccidiosis in a bird, said method comprising administering an effective amount of a vaccine of claim 4 to a bird, thereby inducing resistance to coccidiosis in a bird.

10. A method of inducing resistance to coccidiosis in a bird, said method comprising administering an effective amount of a vaccine of claim 5 to a bird, thereby inducing resistance to coccidiosis in a bird.

* * * * *